United States Patent
Sakata et al.

(10) Patent No.: US 10,987,651 B2
(45) Date of Patent: Apr. 27, 2021

(54) ENDOTOXIN ADSORBENT

(71) Applicants: NATIONAL UNIVERSITY CORPORATION KUMAMOTO UNIVERSITY, Kumamoto (JP); NAGASE CHEMTEX CORPORATION, Osaka (JP)

(72) Inventors: Masayo Sakata, Kumamoto (JP); Towako Sakamoto, Kumamoto (JP); Daisuke Nakamura, Hyogo (JP); Yuki Maeda, Hyogo (JP)

(73) Assignees: National University Corporation Kumamoto University, Kumamoto (JP); Nagase ChemteX Corporation, Osaka (JP)

( * ) Notice: Subject to any disclaimer, the term of this patent is extended or adjusted under 35 U.S.C. 154(b) by 256 days.

(21) Appl. No.: 15/748,542

(22) PCT Filed: Jul. 29, 2016

(86) PCT No.: PCT/JP2016/072347
§ 371 (c)(1),
(2) Date: Jan. 29, 2018

(87) PCT Pub. No.: WO2017/018524
PCT Pub. Date: Feb. 2, 2017

(65) Prior Publication Data
US 2018/0178192 A1 Jun. 28, 2018

(30) Foreign Application Priority Data
Jul. 30, 2015 (JP) .............................. JP2015-151271

(51) Int. Cl.
*B01J 20/24* (2006.01)
*B01D 15/36* (2006.01)
(Continued)

(52) U.S. Cl.
CPC ................. *B01J 20/24* (2013.01); *A61K 9/70* (2013.01); *A61K 47/38* (2013.01); *B01D 15/00* (2013.01);
(Continued)

(58) Field of Classification Search
None
See application file for complete search history.

(56) References Cited

U.S. PATENT DOCUMENTS

2002/0130082 A1* 9/2002 Todokoro ................. B01J 20/26
                                                                  210/660
2003/0127393 A1* 7/2003 Tepper ................... B01D 15/00
                                                                  210/656
(Continued)

FOREIGN PATENT DOCUMENTS

JP          59-112888 A      6/1984
WO    WO-2015/052460 A1    4/2015

OTHER PUBLICATIONS

Todokoro et al., Journal of Liquid Chromatography & Related Technologies, 2002, vol. 25, Issue 4, pp. 601-614.
(Continued)

*Primary Examiner* — Chester T Barry
(74) *Attorney, Agent, or Firm* — Alston & Bird LLP

(57) ABSTRACT

Means for removing endotoxin is provided. Endotoxin is removed by contacting an endotoxin adsorbent including a cellulose nanofiber having an amino group with a liquid containing endotoxin.

13 Claims, 1 Drawing Sheet

(51) Int. Cl.
*A61K 9/70* (2006.01)
*A61K 47/38* (2006.01)
*B01J 20/22* (2006.01)
*B01D 15/00* (2006.01)
*C02F 1/28* (2006.01)
*B01J 20/30* (2006.01)
*B01J 20/26* (2006.01)
*B01J 20/32* (2006.01)
*B01J 20/28* (2006.01)
*C02F 1/42* (2006.01)
*C02F 101/34* (2006.01)

(52) U.S. Cl.
CPC .......... *B01D 15/36* (2013.01); *B01D 15/363* (2013.01); *B01J 20/22* (2013.01); *B01J 20/262* (2013.01); *B01J 20/265* (2013.01); *B01J 20/28004* (2013.01); *B01J 20/28007* (2013.01); *B01J 20/28023* (2013.01); *B01J 20/30* (2013.01); *B01J 20/3085* (2013.01); *B01J 20/3212* (2013.01); *B01J 20/3248* (2013.01); *C02F 1/28* (2013.01); *C02F 1/42* (2013.01); *C02F 2001/422* (2013.01); *C02F 2101/34* (2013.01)

(56) References Cited

U.S. PATENT DOCUMENTS

2007/0213258 A1* 9/2007 Nakayama .......... A61M 1/3672
514/54
2014/0374254 A1* 12/2014 Lauraeus ............... B01D 15/34
204/469

OTHER PUBLICATIONS

Extended European Search Report for corresponding European Application No. 16830627.2 dated Nov. 26, 2018, 10 pages.
Hokkanen et al; Adsorption of Ni(II), Cu(II) and Cd(II) from aqueous solutions by amino modified nanostructured microfibrillated cellulose, Cellulose, vol. 21, Mar. 26, 2014, pp. 1471-1487, XP055278945.
International Search Report for International Patent Application No. PCT/JP2016/072347 dated Oct. 4, 2016, with English translation of the International Search Report, 2 pages.
Morimoto et al., Polymer Journal, 1995, vol. 27, No. 8, pp. 831-839.
Tokodoro et al., Journal of Liquid Chromatography & Related Technologies, 2002, vol. 25, Issue 4, pp. 601-614.
Morimoto et al., Journal of the Chemical Society of Japan, 1994, No. 8, pp. 726-730.

* cited by examiner

[Fig.1]
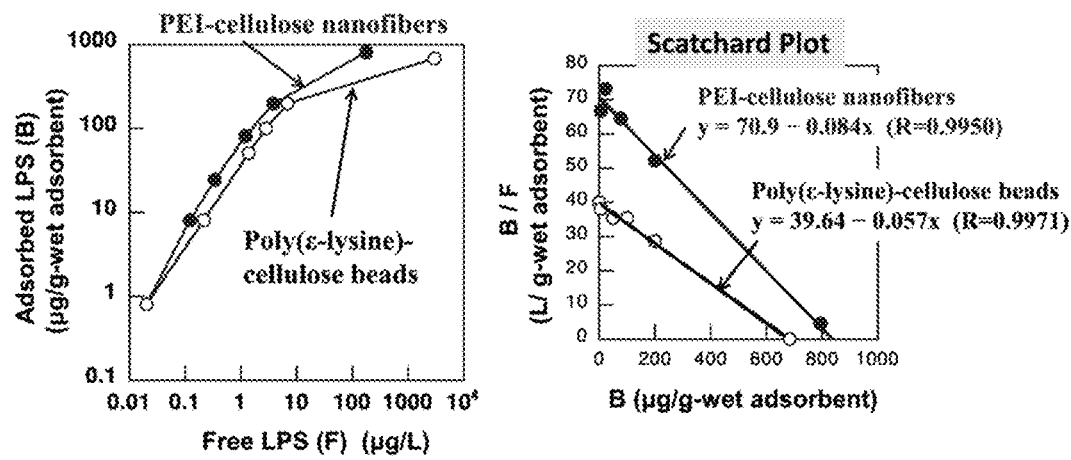
[Fig.2]
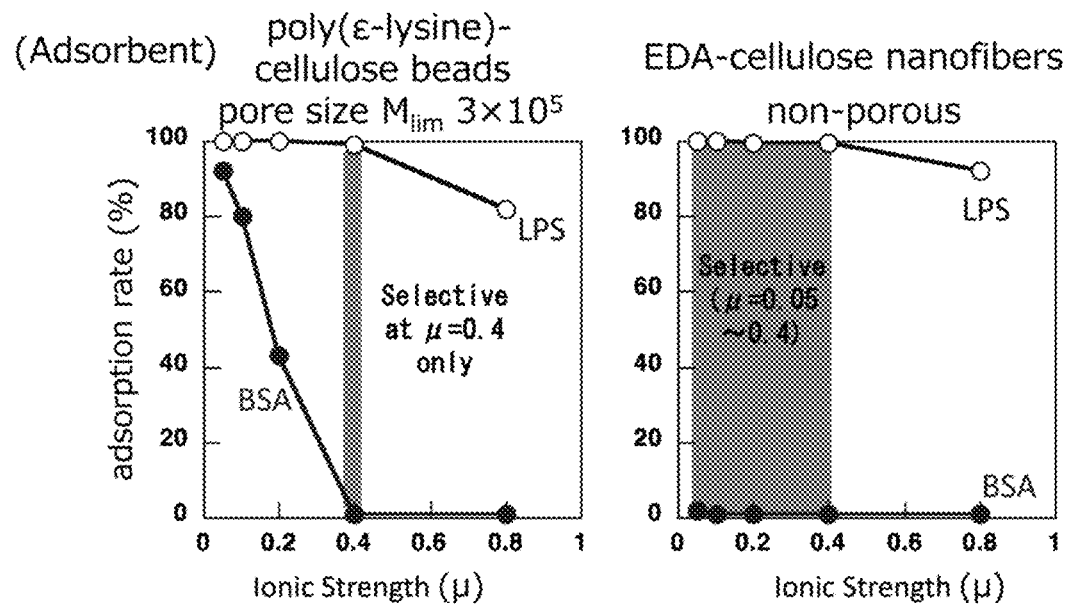

ENDOTOXIN ADSORBENT

CROSS REFERENCE TO RELATED APPLICATIONS

This application is a national phase entry of PCT/JP2016/072347 filed on 29 Jul. 2016, which claims the benefit of and priority to JP Application No. 2015-151271 filed 30 Jul. 2015, the content of which is incorporated herein by reference in its entirety for all purposes.

TECHNICAL FIELD

The present invention relates to an endotoxin adsorbent and an endotoxin removing method using the same.

BACKGROUND

Endotoxin (ET) is one of toxic substances, and, specifically, refers to lipopolysaccharide (LPS) that is a component of an outer membrane of gram-negative bacteria. ET is composed of a polysaccharide and lipid A, where lipid A is mainly responsible for its toxic properties. When ET is taken into a living body due to ET contamination of an injectable solution or the like, it stimulates fever and shock reaction. Therefore, the Japanese Pharmacopoeia defines ET concentration in injectable solutions as being equal to or less than 10 to 100 pg/mL (from 0.1 to 1.0 endotoxin unit (EU)/mL). For example, recent years have seen attempts to isolate and purify DNA from genetically recombinant *Escherichia coli* or the like to use as DNA vaccine. However, DNA thus obtained contains residual ET derived from bacterial cells. Thus, in order to administer the thus-obtained DNA as DNA vaccine to a living body, the residual ET needs to be removed. Accordingly, there has been a strong desire to develop a method for removing ET from various ingredients, e.g. pharmaceutical products such as injectable solutions, and medicinal raw materials such as polymeric materials that serve as raw materials for artificial organs and artificial bones.

A well-known exemplary method for removing ET is to use various ET adsorbents. For example, cationic ET adsorbents, such as poly(ε-lysine)-immobilized cellulose particles (Non-Patent Literature 1), are known as ET adsorbents. However, cationic ET adsorbents form ionic interactions with acidic substances, such as nucleic acids and acidic proteins, and therefore, it has been difficult to selectively remove ET by using a cationic ET adsorbent in the copresence of an acidic substance. Thus, there has been a keen desire for an ET adsorbent capable of selectively removing ET. As ET adsorbents capable of selectively removing ET in the copresence of an acid protein such as BSA, for example, polyethyleneimine-immobilized regenerated cellulose fibers are known (Non-Patent Literature 2).

CITATION LIST

Non-Patent Literature

Non-patent Literature 1: J. LIQ. CHROM. & REL. TECHNOL., 2002, 25(4): 601-614.

Non-Patent Literature 2: Sunao Morimoto et al., Journal of the Chemical Society of Japan, No. 8, pp. 726-730 (1994)

SUMMARY

DETAILED DESCRIPTION

It is an object of the present invention to provide a novel ET adsorbent having high ET adsorption ability.

Means for Solving the Problem

The inventors of the present invention conducted intensive and extensive studies to attain the above object, and consequently found that by introducing an amino group into a cellulose nanofiber, there can be obtained an ET adsorbent having high ET adsorption ability, and particularly, an ET adsorbent exhibiting high selective ET adsorption ability in the copresence of an acidic protein, thereby completing the present invention.

Specifically, the present invention includes the following embodiments.

[1]
An endotoxin adsorbent, comprising:
a cellulose nanofiber having an amino group.

[2]
The endotoxin adsorbent mentioned above, wherein the amount of the amino group in the cellulose nanofiber is from 0.05 to 3.0 meq/dry-g.

[3]
The endotoxin adsorbent mentioned above, wherein the cellulose nanofiber has an average fiber diameter of from 1 to 1000 nm.

[4]
A method for producing the endotoxin adsorbent, the method comprising:
a step of introducing an amino group into a cellulose nanofiber.

[5]
A method for removing endotoxin, the method comprising:
contacting the endotoxin adsorbent mentioned above with a liquid containing endotoxin.

[6]
A method for producing a liquid from which endotoxin has been removed, the method comprising:
contacting the endotoxin adsorbent mentioned above with a liquid containing endotoxin.

[7]
A method for removing endotoxin, the method comprising:
contacting the endotoxin adsorbent mentioned above with a liquid containing a target substance and endotoxin.

[8]
A method for producing a liquid that contains a target substance and from which endotoxin has been removed, the method comprising:
contacting the endotoxin adsorbent mentioned above with a liquid containing the target substance and endotoxin.

[9]
The method mentioned above, wherein the target substance is a substance exhibiting a negative charge.

[10]
The method mentioned above, wherein the target substance is a protein having an isoelectric point of from 4.0 to 10.5.

BRIEF DESCRIPTION OF THE DRAWINGS

FIG. 1 represents charts illustrating ET adsorption isotherms and Scatchard plots regarding Cell-PEI and poly(ε-lysine)-cellulose beads.

FIG. 2 represents charts illustrating ET (LPS) adsorption abilities of Cell-EDA and poly(ε-lysine)-cellulose beads in albumin (BSA)-containing sample solutions having various ionic strengths.

MODE FOR CARRYING OUT THE INVENTION

<1> Endotoxin Adsorbent of the Present Invention and Method for Producing the Same The endotoxin adsorbent (ET adsorbent) of the present invention is an ET adsorbent that comprises a cellulose nanofiber having an amino group. The cellulose nanofiber having an amino group is also referred to as "cellulose nanofiber used in the present invention". ET is also referred to as "LPS".

The term "cellulose nanofiber" refers to fibrous cellulose having an average fiber diameter of nanometer order. The term "cellulose nanofiber" may refer to, specifically, fibrous cellulose having an average fiber diameter of from 1 to 1000 nm. The average fiber diameter of the cellulose nanofiber is not particularly limited as long as it is within the above range. The average fiber diameter of the cellulose nanofiber, for example, may be 1 nm or more, 3 nm or more, 5 nm or more, 10 nm or more, 20 nm or more, or 30 nm or more, may be 1000 nm or less, 500 nm or less, 300 nm or less, 200 nm or less, 150 nm or less, 100 nm or less, 90 nm or less, 80 nm or less, 70 nm or less, 60 nm or less, or 50 nm or less, or may be a combination of any thereof. The average fiber diameter of the cellulose nanofiber may be, specifically, for example, from 3 to 500 nm, from 5 to 300 nm, or from 10 to 200 nm. Additionally, the cellulose nanofiber may have high uniformity in fiber diameter. Specifically, a standard deviation of a fiber diameter distribution of the cellulose nanofiber may be, for example, 100 nm or less, 70 nm or less, 50 nm or less, 40 nm or less, 30 nm or less, or 20 nm or less.

The average fiber length of the cellulose nanofiber is not particularly limited as long as a desired ET adsorption ability can be obtained. The average fiber length of the cellulose nanofiber, for example, may be 5 μm or more, 10 μm or more, 50 μm or more, 100 μm or more, 200 μm or more, 300 μm or more, 500 μm or more, or 1000 μm or more, may be 100000 μm or less, 10000 μm or less, 3000 μm or less, 2500 μm or less, 2000 μm or less, 1500 μm or less, or 1200 μm or less, or may be a combination of any thereof. The average fiber length of the cellulose nanofiber may be, specifically, for example, from 10 to 3000 μm, from 100 to 2500 μm, from 200 to 2000 μm, from 300 to 1500 μm, or from 500 to 1200 μm.

The average aspect ratio of the cellulose nanofiber is not particularly limited as long as a desired ET adsorption ability can be obtained. The term "average aspect ratio" refers to a ratio of average fiber length with respect to average fiber diameter (i.e., average fiber length/average fiber diameter). The average aspect ratio of the cellulose nanofiber, for example, may be 100 or more, 500 or more, 1000 or more, 2000 or more, 3000 or more, 5000 or more, 10000 or more, or 20000 or more, may be 100000 or less, 80000 or less, 50000 or less, 40000 or less, or 35000 or less, or may be a combination of any thereof. The average aspect ratio of the cellulose nanofiber may be, specifically, for example, from 2000 to 100000, from 3000 to 80000, from 5000 to 50000, from 10000 to 40000, or from 20000 to 35000.

It should be noted that the average fiber diameter, the standard deviation of the fiber diameter distribution, the average fiber length, and the average aspect ratio are all calculated based on results of dimensional measurement of at least twenty randomly selected cellulose nanofibers by using an electron microscope.

Additionally, when obtaining an amino group-containing cellulose nanofiber by introducing an amino group into a cellulose nanofiber, the average fiber diameter, the standard deviation of the fiber diameter distribution, the average fiber length, and the average aspect ratio, respectively, may mean the average fiber diameter, the standard deviation of the fiber diameter distribution, the average fiber length, and the average aspect ratio of the cellulose nanofiber before introducing the amino group thereinto. Introducing the amino group into the cellulose nanofiber can result in swelling of the cellulose nanofiber. Thus, for example, the average fiber diameter of the cellulose nanofiber after introducing the amino group can be larger than the average fiber diameter of the cellulose nanofiber exemplified above.

Methods for producing the cellulose nanofiber are not particularly limited. The cellulose nanofiber can be produced, for example, by a known method. The cellulose nanofiber can be obtained, for example, by appropriately processing a cellulose fiber such that a desired average fiber diameter can be obtained. A cellulose fiber that serves as a raw material for use in production of the cellulose nanofiber is also referred to as "raw material fiber".

The origin of the raw material fiber is not particularly limited. Examples of the raw material fiber include higher plant-derived cellulose fibers, animal-derived cellulose fibers, algae-derived cellulose fibers, bacteria-derived cellulose fibers, chemically synthesized cellulose fibers, and derivatives thereof. Examples of the higher plant-derived cellulose fibers include wood fibers such as wood pulp derived from softwood and hardwood; seed hair fibers such as cotton linters, bombax cotton, and kapok; bast fibers such as hemp, mulberry, and mitsumata; vein fibers such as Manila hemp, sisal hemp, and New Zealand hemp; bamboo fibers; and sugar cane fibers. An example of the animal-derived cellulose fiber is sea squirt cellulose. An example of the algae-derived cellulose fiber is Valonia cellulose. An example of the bacteria-derived cellulose fiber is cellulose produced by acetic acid bacteria. Examples of the chemically synthesized cellulose fiber include alkyl celluloses such as methyl cellulose and ethyl cellulose. An example of the derivatives is a cellulose fiber into which a functional group is introduced (substituted). That is, in the present invention, the term "cellulose" includes such a one having a functional group. The type and amount of the functional group to be introduced (substituted) are each not particularly limited as long as the cellulose nanofiber used in the present invention can be produced. Examples of the functional group include amino group and "other functional groups" (functional groups other than amino group) that will be described later.

Examples of a method for producing the cellulose nanofiber from a raw material fiber include a method for producing a cellulose nanofiber by microfibrillating a raw material fiber by using a crusher such as a refiner, a homogenizer, a medium stirring mill, a stone mill, or a grinder (JP-A-2011-026760, JP-A-2012-025833, JP-A-2012-036517, JP-A-2012-036518, and JP-A-2013-236585), a method for producing a cellulose nanofiber by mixing a raw material fiber with a functional particle and kneading the mixture under pressurized conditions (JP-A-2007-262594), a method for producing a cellulose nanofiber by dissociating a raw material fiber in a wet process, then preliminarily defibrating, steam-treating, and microfibrillating by using a crusher, wherein an enzyme is used in combination (JP-A-2008-075214), and a method for producing a cellulose nanofiber by dissociating a raw material fiber in a wet process, then preliminarily defibrating, and microfibrillating by ultrasonic treatment, wherein an enzyme is used in combination (JP-A-2008-169497).

Additionally, the cellulose nanofiber can also be produced by spinning, for example, from a cellulose-ionic liquid solution or a cellulose-organic solvent solution (JP-A-2015-004151 and JP-A-2009-203467).

In addition, as the cellulose nanofiber, for example, a cellulose fiber inherently having such an average fiber diameter as described above can also be used as it is or after being processed as appropriate. Examples of the cellulose fiber inherently having such an average fiber diameter as described above include celluloses produced by acetic acid bacteria.

Furthermore, a commercially available product can also be used as the cellulose nanofiber. Examples of the commercially available cellulose nanofiber include CELISH (registered trademark) manufactured by Daicel FineChem Ltd., and CELLULON (registered trademark) manufactured by CP Kelco U.S., Inc. Examples of CELISH include KY-100S, KY-100G, KY-110N, and KY-1005.

The cellulose nanofiber used in the present invention has an amino group ($-NH_2$). The cellulose nanofiber used in the present invention may inherently have an amino group or may be a cellulose nanofiber modified so as to have an amino group. The cellulose nanofiber modified so as to have an amino group is also referred to as "aminated cellulose nanofiber". The aminated cellulose nanofiber can be obtained, for example, by introducing an amino group into a cellulose nanofiber. Methods for introducing an amino group into a cellulose nanofiber are not particularly limited. An amino group can be introduced into a cellulose nanofiber, for example, by a known method for introducing an amino group into cellulose.

For example, an amino group can be introduced into a hydroxyl group of cellulose. The introduction of an amino group into a hydroxyl group thereof can be performed, for example, by a known method. An example of the method for introducing an amino group into a hydroxyl group of cellulose is a method in which a hydroxyl group of cellulose is activated by an activator and then reacted with an amino group donor (JP-A-2003-048902 and JP-A-2009-167307). Examples of the activator include chloromethyl oxirane (epichlorohydrin), p-toluene sulfonic acid chloride, and 2-fluoro-1-methylpyridinium. Examples of the amino group donor include those described later, such as polyethyleneimine and ethylenediamine. Specifically, for example, a hydroxyl group of cellulose can be epoxidized with chloromethyl oxirane and then reacted with polyethyleneimine or ethylenediamine to obtain cellulose having an amino group introduced into the hydroxyl group (see Examples). Additionally, for example, an amino group can be selectively introduced into a specific hydroxyl group of cellulose. An example of the specific hydroxyl group of cellulose is a hydroxyl group at position 6 of cellulose. For example, cellulose having an amino group introduced into the hydroxyl group at position 6 can be produced via a 6-tosylated cellulose derivative or 6-oxidized cellulose derivative (Carbohydrate Research, 340(2005) 1403-1406; Carbohydrate Research, 208(1990) 183-191; and JP-A-2009-293017). Specifically, for example, the hydroxyl group at position 6 of cellulose can be selectively tosylated with p-toluene sulfonic acid chloride under certain conditions, the p-toluenesulfonyl group can be azidated, and the azide group can be reduced to obtain cellulose in which the hydroxyl group at position 6 is substituted with an amino group (JP-A-2009-293017).

Examples of the amino group donor include ammonia and amines. Examples of the amines include monovalent amines (amines having one amino group) and polyvalent amines (amines having two or more amino groups). Examples of the monovalent amines include alkylamines such as methylamine, ethylamine, dimethylamine, and diethylamine; amino alcohols such as methanol amine, ethanol amine, methyl ethanol amine, ethyl ethanol amine, dimethyl ethanol amine, and diethyl ethanol amine; and aromatic amines such as aniline. Examples of the polyvalent amines include aliphatic diamines such as ethylenediamine, tetramethylenediamine, and hexamethylenediamine; alicyclic diamines such as 4,4'-diamino-3,3' dimethyl dicyclohexylmethane, diamine cyclohexane, and isophorone diamine; aromatic diamines such as phenylenediamine, diaminonaphthalene, and xylylenediamine; trivalent or more polyvalent aliphatic amines such as diethylenetriamine, triethylenetetramine, tetraethylenepentamine, tris(2-aminoethyl)amine, and tris(3-aminopropyl) amine; trivalent or more polyvalent aromatic amines such as melamine; and polymers having an amino group, such as polyethyleneimine, polyvinylamine, and polyallylamine. Such polymers may be straight-chained (linear type) or branched (branched type). The number-average molecular weight of such polymers is not particularly limited. The number-average molecular weight of such polymers, for example, may be 200 or more, 300 or more, or 400 or more, may be 1,000,000 or less, 100,000 or less, 10,000 or less, 5,000 or less, 2,000 or less, 1,000 or less, or may be a combination of any thereof. The number average molecular weight of such polymers may be, for example, from 400 to 100,000. Particular examples of the polyvalent amines include polyethyleneimine, ethylenediamine, diethylenetriamine, triethylenetetramine, tetraethylenepentamine, and pentaethylenehexamine. As the amino group donor, one kind of amino group donor may be used, or two or more kinds of amino group donors may be used.

In addition, another example of the method for introducing an amino group into cellulose is a method in which an epoxy group donor such as glycidyl methacrylate or glycidyl acrylate is introduced into cellulose by graft reaction, and then, an amino group donor such as ammonia or amine is reacted with the epoxy group.

The contained amount of the amino group in the cellulose nanofiber used in the present invention is not particularly limited as long as a desired ET adsorption ability can be obtained. The contained amount of the amino group in the cellulose nanofiber, in terms of an anion exchange capacity (AEC), for example, may be 0.01 meq/dry-g or more, 0.03 meq/dry-g or more, 0.05 meq/dry-g or more, 0.07 meq/dry-g or more, 0.1 meq/dry-g or more, 0.3 meq/dry-g or more, or 0.5 meq/dry-g or more, may be 10.0 meq/dry-g or less, 5.0 meq/dry-g or less, 3.0 meq/dry-g or less, 2.5 meq/dry-g or less, 2.0 meq/dry-g or less, 1.5 meq/dry-g or less, 1.2 meq/dry-g or less, or 1.0 meq/dry-g or less, or may be a combination of any thereof. Specifically, the contained amount of the amino group in the cellulose nanofiber, in terms of an anion exchange capacity (AEC), may be, for example, from 0.05 to 3.0 meq/dry-g, from 0.1 to 2.0 meq/dry-g, or from 0.5 to 1.0 meq/dry-g.

The cellulose nanofiber used in the present invention may further have a functional group other than amino group (hereinafter also referred to as "other functional group") as long as a fiber form can be maintained and a desired ET adsorption ability can be obtained. The cellulose nanofiber used in the present invention may inherently have the other functional group or may be a cellulose nanofiber modified so as to have the other functional group. Examples of the other functional group include an alkyl group, an alkoxy group, an epoxy group, a carboxyl group, a hydroxyl group, a phosphoric acid group, a sulfuric acid group, a formyl group, an acetyl group, hydrogen, and halogen. Examples of the alkyl group include alkyl groups having 1 to 10 carbon atoms, 1 to 7 carbon atoms, 1 to 5 carbon atoms, or 1 to 3 carbon atoms. The alkyl group may be linear or may be branched. Examples of the alkoxy group include alkoxy groups having 1 to 10 carbon atoms, 1 to 7 carbon atoms, 1 to 5 carbon atoms, or 1 to 3 carbon atoms. The alkoxy group may be linear or may be branched. Hydrogen atoms of the alkyl group and the alkoxy group may be each independently substituted with another functional group, for example, the other functional group such as those exemplified above or an amino group. Examples of the halogen include fluorine, chlorine, bromine, and iodine. In the cellulose nanofiber used in the present invention, for example, a part or all of hydroxyl groups inherently contained in the cellulose nanofiber may remain, or a part of functional groups, such as epoxy groups, used to introduce an amino group may remain. The cellulose nanofiber used in the present invention may have one kind of other functional group or may have two or more kinds of other functional groups.

The contained amount of the other functional group in the cellulose nanofiber used in the present invention is not particularly limited as long as a fiber form can be maintained and a desired ET adsorption ability can be obtained. For example, when a substance having a negative charge, such as an acidic substance, is present in a sample to be treated with the ET adsorbent of the present invention, the contained amount of an anion exchange group other than the amino group in the cellulose nanofiber used in the present invention may be preferably small, from the viewpoint of reducing nonspecific adsorption of the substance having a negative charge. The contained amount of the anion exchange group other than the amino group in the cellulose nanofiber used in the present invention may be, in terms of an anion exchange capacity (AEC), for example, 1 meq/g or less, 0.7 meq/g or less, 0.5 meq/g or less, 0.3 meq/g or less, 0.1 meq/g or less, 0.05 meq/g or less, or 0 (zero). Additionally, for example, when a substance having a positive charge, such as a basic substance, is present in a sample to be treated with the ET adsorbent of the present invention, the contained amount of a cation exchange group in the cellulose nanofiber used in the present invention may be preferably small, from the viewpoint of reducing nonspecific adsorption of the substance having a positive charge. The contained amount of the anion exchange group in the cellulose nanofiber used in the present invention may be, in terms of a cation exchange capacity (CEC), for example, 1 meq/g or less, 0.7 meq/g or less, 0.5 meq/g or less, 0.3 meq/g or less, 0.1 meq/g or less, 0.05 meq/g or less, or 0 (zero).

The ion exchange capacities can be quantified by a pH titration method. A specific procedure for quantifying an ion exchange capacity by pH titration can be obtained, for example, by referring to the description of Examples.

The cellulose nanofiber used in the present invention may have a large ET adsorption capacity. The ET adsorption capacity of the cellulose nanofiber used in the present invention may be, for example, 500 μg or more, 700 μg or more, 800 μg or more, or 850 μg or more, per wet-g. Additionally, the cellulose nanofiber used in the present invention may have a small apparent ET dissociation constant. The apparent ET dissociation constant of the cellulose nanofiber used in the present invention may be, for example, $2.0 \times 10^{-11}$ M or less, $1.7 \times 10^{-11}$ M or less, $1.5 \times 10^{-11}$ M or less, or $1.3 \times 10^{-11}$ M or less. The ET adsorption capacity and the apparent ET dissociation constant can be calculated from a linear equation obtained by a Scatchard plot created based on an ET adsorption isotherm. A specific procedure for calculating ET adsorption capacity and an apparent ET dissociation constant in such a way above can be obtained, for example, by referring to the description of the Examples.

The cellulose nanofiber having an amino group can be dispersed and stored in an appropriate dispersion medium such as methanol or ethanol.

The cellulose nanofiber having an amino group can be used solely or in combination with other constituent element(s), as the ET adsorbent of the present invention. That is, the ET adsorbent of the present invention may consist only of the cellulose nanofiber having an amino group or may further comprise other constituent element(s). The other constituent element(s) is/are not particularly limited as long as a desired ET adsorption ability can be obtained.

The obtained ET adsorbent of the present invention can be made ET-free as appropriate, and then used. An ET-free form can be obtained by a usual method. Specifically, an ET-free form can be obtained, for example, by washing the ET adsorbent of the present invention once or plural times with an appropriate cleaning liquid. The cleaning liquid is not particularly limited, and examples thereof include an NaOH aqueous solution and an NaOH ethanol solution. After washing, the ET adsorbent of the present invention can be separated from the cleaning liquid by an appropriate solid-liquid separating means, such as centrifugation or filtration.

The ET adsorbent of the present invention may be provided as it is or after being subjected to a treatment, such as processing, as appropriate. For example, the ET adsorbent of the present invention may be provided in a form suitably usable in an ET removing method of the present invention. For example, the ET adsorbent of the present invention can be used after being processed into an arbitrary form, such as a particle form or a membrane form. Additionally, for example, the ET adsorbent of the present invention can be used after being filled into a column. Specifically, the ET adsorbent of the present invention may be, for example, filled into a column and provided as a column for ET removal. That is, the present invention provides a column for ET removal, the column containing the ET adsorbent of the present invention filled thereinto.

<2> Use of ET Adsorbent of the Present Invention

ET can be removed by using the ET adsorbent of the present invention. That is, the present invention provides a method for removing ET, the method comprising contacting the ET adsorbent of the present invention with a liquid containing ET. The method is also referred to as "ET removing method of the present invention". The "liquid containing ET" is also referred to as "ET-containing liquid". A liquid from which ET has been removed can be obtained by the ET removing method of the present invention. That is, the ET removing method of the present invention may also be a method for producing a liquid from which ET has been removed, the method comprising contacting the ET adsorbent of the present invention with an ET-containing liquid.

The ET-containing liquid is not particularly limited as long as it is a liquid containing ET. The ET-containing liquid may further contain a substance other than ET, in addition to ET. Examples of the liquid include water, solutions such as an aqueous solution, and suspensions such as an aqueous suspension. An example of the water is medicinal water such as injection water.

In an embodiment of the present invention, when the ET-containing liquid contains ET and a substance other than ET, ET can be selectively removed from the ET-containing liquid, that is, ET can be separated from the substance other than ET. The "substance other than ET" to be separated from ET is also referred to as "target substance". That is, an embodiment of the ET removing method of the present invention is a method for removing ET, the method comprising contacting the ET adsorbent of the present invention with a liquid containing a target substance and ET. A liquid that contains a target substance and from which ET has been removed can be obtained by an embodiment of the ET removing method of the present invention. That is, an embodiment of the ET removing method of the present invention may also be a method for producing a liquid that contains a target substance and from which ET has been removed, the method comprising contacting the ET adsorbent of the present invention with a liquid containing the target substance and ET. Additionally, a target substance from which ET has been removed can be obtained by collecting the target substance from the liquid obtained by an embodiment of the ET removing method of the present invention, which liquid contains the target substance and from which ET has been removed. That is, an embodiment of the ET removing method of the present invention may be a method for producing a target substance from which ET has been removed, the method comprising contacting the ET adsorbent of the present invention with a liquid containing the target substance and ET and collecting the target substance.

The ET-containing liquid may be a liquid inherently containing a target substance and ET or may be a liquid prepared by dissolving or suspending a target substance contaminated with ET in a liquid medium. The ET-containing liquid may contain one kind of target substance or may contain two or more kinds of target substances.

The target substance is not particularly limited. The ET adsorbent of the present invention can be particularly used to selectively remove ET in the copresence of a substance exhibiting a negative charge or a viscous substance. Thus, examples of the target substance include, for example, substances exhibiting a negative charge and viscous substances. Additionally, examples of the target substance also include active ingredients contained in pharmaceutical products such as injectable solutions, and medicinal raw materials such as polymeric materials that serve as raw materials for artificial organs and artificial bones. These target substances each may also belong to two or more categories. For example, the target substances may be a viscous substance exhibiting a negative charge or may be an active ingredient or medicinal raw material exhibiting a negative charge or viscosity.

The term "substance exhibiting a negative charge" refers to a substance having a functional group that tends to become an anion in a molecule thereof. The term "functional group that tends to become an anion" refers to a functional group that can become an anion in an arbitrary liquid containing a substance having the functional group. Specifically, for example, a functional group that can become an anion in an ET-containing liquid is a "functional group that tends to become an anion". That is, the term "substance exhibiting a negative charge" may refer to a substance exhibiting a negative charge in an arbitrary liquid containing the substance, e.g., in the ET-containing liquid. Examples of the "functional group that tends to become an anion" include acidic groups such as a carboxyl group, a sulfate group, and a phosphate group. That is, examples of the "substance exhibiting a negative charge" include, for example, acidic substances. Examples of the "substances exhibiting a negative charge" include, for example, proteins, peptides, hormones, polysaccharides, nucleic acids, lipids, vitamins, and artificial polymers, each of which exhibits a negative charge. Examples of the proteins and peptides exhibiting a negative charge include proteins and peptides containing an acidic amino acid residue. Examples of the acidic amino acid residue include, for example, a glutamine acid residue and an asparagine acid residue. The term "protein or peptide exhibiting a negative charge" may mean, for example, a protein or peptide having an isoelectric point of from 4.0 to 10.5. In the ET removing method of the present invention, it is preferable that ET can be selectively removed, for example, in the copresence of a protein or peptide having an isoelectric point of from 4.0 to 10.5. Examples of the protein having an isoelectric point of from 4.0 to 10.5 include bovine serum albumin (BSA), globulin, myoglobin, and lysozyme. Examples of the polysaccharides exhibiting a negative charge include polyanion derivatives of polysaccharides, such as polyanion derivatives of cellulose, amylose, pullulan, starch, and dextrin; and glycosaminoglycans such as heparin, hyaluronic acid, and chondroitin sulfate. Examples of the polyanion derivatives of cellulose include carboxymethyl cellulose and cellulose sulfate. Nucleic acids are acidic substances containing a large amount of phosphate ester in a molecule thereof, and examples of the nucleic acids include DNA and RNA. Examples of the artificial polymers exhibiting a negative charge include polyacrylic acids. These "substances exhibiting a negative charge" each may be a natural product, e.g., a living body-derived substance, or may be an artificially modified or synthesized substance.

Examples of the "viscous substances" include, for example, fibrous viscous polymers. Examples of the fibrous viscous polymers include polysaccharides exhibiting a negative charge and fibrous proteins such as collagen and gelatin.

In the ET removing method of the present invention, the ET-containing liquid may be subjected to a treatment such as a pre-treatment, as appropriate, before contacting with the ET adsorbent of the present invention. For example, the ET-containing liquid may be contacted with the ET adsorbent of the present invention after being diluted or concentrated. The pH of the ET-containing liquid may be or may not be adjusted. The pH of the ET-containing liquid is not particularly limited as long as ET can be removed. The pH of the ET-containing liquid may be, for example, from 3 to 10, preferably from 4 to 9, and more preferably from 4 to 6. The pH of the ET-containing liquid may be adjusted, for example, in consideration of stability of the target substance at each pH. Adjustment of the pH can be performed, for example, by using a buffer solution. The kind of the buffer solution is not particularly limited, and can be appropriately selected according to various conditions such as a desired pH. Additionally, the ionic strength of the ET-containing liquid may be or may not be adjusted. The ionic strength ($\mu$) of the ET-containing liquid is not particularly limited as long as ET can be removed. The ionic strength ($\mu$) of the ET-containing liquid may be, for example, from 0.05 to 0.8, from 0.05 to 0.6, or from 0.05 to 0.4.

The ET adsorbent of the present invention may be used as it is or after being subjected to a treatment, such as processing, as appropriate. For example, the ET adsorbent of the present invention can be filled in a column, and then used.

Means for contacting the ET adsorbent of the present invention with the ET-containing liquid are not particularly limited. The means for contacting the ET adsorbent of the present invention with the ET-containing liquid can be appropriately selected according to various conditions such as embodiments of the ET adsorbent of the present invention and embodiments of the ET-containing liquid. The ET adsorbent of the present invention can be contacted with the ET-containing liquid, for example, by referring to known means for processing a liquid sample by a solid carrier.

The ET adsorbent of the present invention can be contacted with the ET-containing liquid, for example, by a batch method. The term "batch method" refers to a method in which the ET adsorbent of the present invention and the ET-containing liquid are mixed together in an appropriate container, so that the ET adsorbent of the present invention is contacted with the ET-containing liquid. That is, for example, the ET adsorbent of the present invention can be added into the ET-containing liquid, and thereby the ET adsorbent of the present invention can be contacted with the ET-containing liquid. The batch method may be performed under static conditions or with stirring or shaking. By allowing the ET adsorbent of the present invention to adsorb ET and then removing the ET adsorbent of the present invention from the mixture, there can be obtained a liquid from which ET has been removed.

Additionally, the ET adsorbent of the present invention can be contacted with the ET-containing liquid, for example, by a fluidizing separation method. The term "fluidizing separation method" refers to a method in which the ET-containing liquid is allowed to pass through the ET adsorbent of the present invention, so that the ET adsorbent of the present invention is contacted with the ET-containing liquid. That is, for example, when the ET adsorbent of the present invention is filled into a column and used, the ET-containing liquid can be allowed to pass through the column filled with the ET adsorbent of the present invention, and thereby the ET adsorbent of the present invention can be contacted with the ET-containing liquid (a column method). Additionally, for example, when the ET adsorbent of the present invention is formed as a filter, the ET-containing liquid can be allowed to pass through the filter, and thereby the ET adsorbent of the present invention can be contacted with the ET-containing liquid. Examples of the fluidizing separation method include such methods as: chromatographies such as liquid chromatography, membrane chromatography, and monolith chromatography; filtration using a hollow fiber membrane, a tubular membrane, a flat membrane, a membrane filter, filter paper, or the like; solid phase extraction; and purification of a sample such as a body fluid by using an adsorption column.

In the ET removing method of the present invention, the treatment speeds, i.e., the time of contact between the ET adsorbent of the present invention and the ET-containing liquid in the batch method and the flow rate (a liquid passing speed) of the ET-containing liquid in the fluidizing separation method, are not particularly limited as long as ET can be removed. The treatment speeds can be appropriately set, for example, according to various conditions such as the contained amounts of ET and a target substance in the ET-containing liquid and the kind of the target substance. The time of the contact may be, for example, from 5 minutes to 120 hours, from 30 minutes to 24 hours, from 1 to 12 hours, or from 2 to 4 hours. The liquid passing speed may also be set equivalently. Additionally, in the ET removing method of the present invention, the treatment temperature is not particularly limited as long as ET can be removed. The treatment temperature can be appropriately set, for example, according to various conditions such as the kind of the target substance. The treatment temperature may be, for example, from 5 to 80° C., from 15 to 65° C., or from 25 to 50° C.

ET in an ET-containing liquid is removed by the ET removing method of the present invention. The degree of removal of ET is not particularly limited as long as the contained amount of ET in the liquid after treatment (i.e. after contacting with the ET adsorbent of the present invention) is reduced as compared to that before treatment (i.e. before contacting with the ET adsorbent of the present invention). The expression "ET is removed" may mean, for example, that the contained amount of ET in the liquid after the treatment is reduced to 30% or less, 20% or less, 10% or less, 5% or less, 2% or less, or 1% or less as compared to that before the treatment. Additionally, the expression "ET is removed" may mean, for example, that the contained amount of ET in the liquid after the treatment becomes 0.5 EU/mL or less, 0.2 EU/mL or less, 0.1 EU/mL or less, 0.05 EU/mL or less, 0.02 EU/mL or less, 0.01 EU/mL or less, 0.005 EU/mL or less, 0.002 EU/mL or less, or 0.001 EU/mL or less. Particularly, in the ET removing method of the present invention, it is preferable that ET can be removed from a dilute ET-containing liquid. For example, ET may be removed from an ET-containing liquid that contains ET in an amount of 40 EU/mL or less, 30 EU/mL or less, 20 EU/mL or less, or 10 EU/mL or less such that the contained amount of ET becomes such a contained amount of ET in the liquid after the treatment as exemplified above, e.g. 0.1 EU/mL or less. Additionally, when ET is separated from a target substance, the target substance is allowed to remain in the liquid after the treatment. The degree of residual of the target substance is not particularly limited as long as a desired amount of the target substance remains in the liquid after the treatment. It is preferable that the target substance is substantially not removed. The expression "a target substance is substantially not removed" may mean, for example, that the contained amount of the target substance in the liquid after the treatment is maintained to be 90% or more, 95% or more, 97% or more, or 99% or more as compared to that before the treatment.

Removal of ET can be confirmed by quantifying ET in the liquid after the treatment. An Example of ET quantifying methods is a Limulus test using a Limulus reagent. The Limulus test can be performed by a usual method. The Limulus test can be performed, for example, by a colorimetric method, a turbidimetric method, or a gelation method.

Examples

Hereinafter, the present invention will be described more specifically by using Examples. However, the present invention is not limited thereto.

<1> Production of Aminated Cellulose Nanofiber

As aminated cellulose nanofibers, a polyethyleneimine (PEI)-immobilized cellulose nanofiber and an ethylenediamine (EDA)-immobilized cellulose nanofiber were synthesized by the following procedures.

In a 500 mL separable flask, 20 wet-g of a wet cellulose nanofiber (CELISH KY-100S; Lot. 64011; manufactured by Daicel FineChem Ltd.,) and a 10% (w/w) aqueous sodium hydroxide solution (prepared by dissolving 10 g of sodium hydroxide (special grade; manufactured by Nacalai Tesque, Inc.,) in 90 mL of water) were placed, and the resulting mixture was stirred for 1 hour in a 30° C. water bath. Next, 160 mL of chloromethyl oxirane (special grade; manufactured by Wako Pure Chemical Industries, Ltd.,) was added into the separable flask, and the resulting mixture was further stirred for 2 hours in the 30° C. water bath. The stirring speed was kept constant. The reaction product was suction-filtered on a filter cloth (Toray's SILK, mesh size: 20 μm, manufactured by Toray Industries, Ltd.,), to obtain an epoxy-activated cellulose nanofiber as a solid content (a filtrate residue). The obtained epoxy-activated cellulose nanofiber and a 30% (v/v) PEI aqueous solution (a mixture solution of 30 mL of PEI (linear; number-average molecular weight: about 423; manufactured by Aldrich Corp.,) and 70 mL of water) were placed in a separable flask and stirred for 4 hours in a 45° C. water bath. The reaction product was thoroughly washed with ultrapure water on Tray's SILK until a pH of the washing solution became nearly neutral, to obtain a PEI-immobilized cellulose nanofiber (hereinafter also referred to as "Cell-PEI" or "PEI-cellulose nanofiber (s)" as a solid content (a filtrate residue). It is to be noted that while data regarding the Cell-PEI are described in the following AEC measurement and evaluation of ET (LPS) adsorption ability, PEI-immobilized cellulose nanofibers were separately synthesized by using some branched-type PEIs (number-average molecular weight: from 500 to 78,000) and confirmed to exhibit ET(LPS) adsorption ability as with the Cell-PEI.

In addition, synthesis was performed in the same procedure by using CELISH KY-100S (Lot. 64011; manufactured by Daicel Finechem Ltd.,) with a 30% (v/v) EDA aqueous solution (a mixture solution of 30 mL of EDA (manufactured by Wako Pure Chemical Industries, Ltd.) and 70 mL of water) in place of the 30% (v/v) PEI aqueous solution to obtain an EDA-immobilized cellulose nanofiber (hereinafter also referred to as "Cell-EDA" or "EDA-cellulose nanofiber(s)".

Parts of the aminated cellulose nanofibers thus obtained were collected for AEC measurement, and the rests thereof were dispersed in methanol and refrigerated for preservation until use.

<2> AEC Measurement

Anion exchange capacity (AEC) of the synthesized aminated cellulose nanofibers was measured to determine the amount of an amino group introduced into the aminated cellulose nanofibers. That is, AEC measurement can determine the amount of introduction of a primary amine ($-NH_2$), which is a terminal group. The AEC was measured by a back-titration method. The procedure will be given below.

Each aminated cellulose nanofiber was dried under reduced pressure for 24 hours or more, weighed precisely, and placed in an Erlenmeyer flask. A 30 ml aliquot of 0.1 mol/l hydrochloric acid with a known factor was added thereto, and the flask was shaken for 2 hours on a shaker (at 200 rpm at 25° C.). The resulting mixture was filtered through a filter paper, and 20 ml of the filtrate was diluted to 100 ml with distilled water. A 10 ml aliquot of the diluted solution was placed into another Erlenmeyer flask and titrated with 0.05 mol/l sodium hydroxide with a known factor by using phenolphthalein as an indicator. The AEC of the each aminated cellulose nanofiber was calculated by the following formula (I). As a result, the AEC of the Cell-PEI was 0.64 (meq/dry-g), and the AEC of the Cell-EDA was 0.83 (meq/dry-g).

$$\text{AEC (meq/dry-g)} = (0.1 \times f_{HCl} \times 30 - 0.05 \times f_{NaOH} \times V \times 30/20 \times 100/10) \div W \quad (I)$$

$f_{HCl}$: Factor of hydrochloric acid used
$f_{NaOH}$: Factor of aqueous sodium hydroxide solution used
V: Amount of titration (ml)
W: Particle dry weight (dry-g)

<3> Evaluation of ET (LPS) Adsorption Ability

ET adsorption ability of the synthesized aminated cellulose nanofibers was measured and compared with the ET adsorption ability of a known ET adsorbent. As the known ET adsorbent, cellulose-polylysine (J. LIQ CHROM. & REL. TECHNOL., 2002, 25(4): 601-614.) was used. The cellulose-polylysine consists of poly(ε-lysine)-immobilized cellulose particles (AEC=0.45 meq/g). Hereinafter, cellulose-polylysine will also be referred to as "poly(ε-lysine)-cellulose beads".

<3-1> Evaluation Method

Evaluation of ET adsorption ability was performed by the batch method. Procedure will be given below.

Glassware (Erlenmeyer flasks, graduated pipettes, vials, Limulus tubes, tube caps, and spatulas) was thoroughly washed, then sufficiently dried by using a drier, and sterilized at 250° C. for 4 hours prior to use. Syringes, membrane filters, and tips used were products preliminarily sterilized by gamma-ray irradiation. Pure water was sterilized at 120° C. for 30 minutes in an autoclave prior to use.

For measurement of ET concentration, 0.2 ml of a buffer solution attached to a commercially available Limulus reagent, Endospecy ES-24S (a set including 24 test tubes containing a freeze-dried product of Limulus amebocyte lysate, manufactured by Seikagaku Corporation) was added per test tube of the Limulus reagent to dissolve the content.

Each adsorbent was washed 5 times with 25 ml of 0.2M NaOH in 95% EtOH on a glass filter. Next, washing with sterilized pure water was repeatedly performed until the filtrate became neutral. Then, washing with 25 mL of a phosphate buffer solution (pH 6, ionic strength μ=0.2) was performed twice.

The washed each adsorbent was weighed and placed in a 20 ml Erlenmeyer flask. A phosphate buffer solution (pH 6; ionic strength μ=0.2) containing endotoxin having a predetermined concentration (*E coli* 055:B5-derived EVV Endotoxin, manufactured by Wako Pure Chemical Industries, Ltd.,) was added thereinto, and the flask was shaken at from 25 to 50° C. at 200 rpm for from 2 to 4 hours in an incubator. Next, the adsorbent-containing solution was sucked by a syringe and filtered through a 0.8 μm membrane filter. The filtrate was diluted to 100 times with Otsuka water (LPS-free distilled water, manufactured by Otsuka Pharmaceutical Co., Ltd). A 0.2 ml aliquot of the diluted solution was added into the test tube containing the Limulus reagent described above, and mixed thoroughly by a vortex mixer. The test tube was placed in an EG-reader SV-12 (manufactured by Seikagaku Corporation), and the residual ET concentration was determined by a colorimetric time method.

<3-2> Comparisons of ET Adsorption Capacity and ET Dissociation Constant

Regarding each adsorbent (Cell-PEI and poly(ε-lysine)-cellulose beads), ET adsorption tests were performed by the batch method using sample solutions having various ET concentrations (from 1 to 10000 EU/mL, pH: 7.0, μ=0.05), to create an ET adsorption isotherm of each adsorbent. In the batch method, 0.1 wet-g of the adsorbent and 4 mL of the sample solution were used. A Scatchard plot was calculated from the adsorption isotherm. Results are shown in FIG. 1. From a linear equation obtained by the Scatchard plot, the apparent dissociation constant between the each adsorbent and ET, and the adsorption capacity were calculated.

That is, the adsorbed endotoxin amount B (μg/g wet adsorbent) was plotted on a y-axis and the residual endotoxin concentration F (μg/L) was plotted on an x-axis, to obtain a left graph in FIG. 1. The B was plotted on the x-axis and the B/F ratio was plotted on the y-axis, to obtain a right graph (Scatchard plot) in FIG. 1, whereby a linear equation y=ax+b was obtained for each adsorbent. When the associated molecular weight of endotoxin is assumed to be $10^6$, the dissociation constant and adsorption capacity can be expressed by the following equation:

Apparent endotoxin dissociation constant=$1/|a|\times10^{12}$

Endotoxin adsorption capacity (μg/wet-g of adsorbent)=$-(b/a)$

As a result, the LPS adsorption capacity per wet-g of the Cell-PEI (AEC=0.64 meq/g) was 884 μg (=$4.4\times10^5$ EU), and the dissociation constant thereof was $1.2\times10^{-11}$ M. On the other hand, the LPS adsorption capacity per wet-g of the poly(ε-lysine)-cellulose beads was 695 μg (=$3.5\times10^5$ EU), and the dissociation constant thereof was $1.8\times10^{-11}$ M. That is, the results showed that the LPS adsorption capacity of the Cell-PEI was higher (1.34 times) than that of the poly(ε-lysine)-cellulose beads, and the dissociation constant of the Cell-PEI was lower (0.66 times) than that of the poly(ε-lysine)-cellulose beads. It is preferable that the LPS adsorption capacity of an adsorbent is large, and that the LPS dissociation constant thereof is small since LPS can be removed from a dilute LPS solution. Thus, the ET adsorption ability of the Cell-PEI was shown to be preferable to that of the poly(ε-lysine)-cellulose beads.

<3-3> Evaluation of Selective ET(LPS) Adsorption Ability in Albumin (BSA) Solution Regarding each adsorbent (Cell-EDA and poly(ε-lysine)-cellulose beads), ET adsorption tests were performed by the batch method using albumin (BSA)-containing sample solutions having various ionic strengths (albumin (BSA): 500 μg/mL, LPS (*E. Coli* UKT-B): 25 EU/mL, pH: 7.0), to evaluate selective ET (LPS) adsorption ability. In the batch method, 0.2 wet-g of the adsorbent and 2 mL of the sample solution were used. The temperature was 25° C., and the reaction time (stirring time) was 2 hours. Albumin (BSA) was quantified based on absorbance at a BSA peak (280 nm) obtained by performing UV measurement of each sample solution by a UV-vis spectrophotometer (GeneQuant 1300, manufactured by GE Healthcare Japan Corporation). Results are shown in FIG. 2. The Cell-EDA exhibited high selectivity to LPS without adsorbing protein at any ionic strength (μ), and particularly exhibited high effects (LPS adsorption rate: 99%, residual LPS concentration: <0.1 EU/mL) at an ionic strength μ=from 0.05 to 0.4. On the other hand, the poly(ε-lysine)-cellulose beads exhibited high LPS adsorption ability (LPS adsorption rate 99%) at ionic strengths μ=from 0.05 to 0.4, but exhibited low LPS selectivity. The reason for this seems to be that, in the poly(ε-lysine)-cellulose beads, BSA is adsorbed by pores. Thus, the Cell-EDA was shown to have higher selective ET adsorption ability than the poly(ε-lysine)-cellulose beads.

Additionally, regarding each adsorbent (Cell-PEI, Cell-EDA, and poly(ε-lysine)-cellulose beads), ET adsorption tests were performed by the batch method using an albumin (BSA)-containing sample solution under conditions described in Table 1, to evaluate selective ET(LPS) adsorption ability. In the batch method, 0.2 wet-g of the adsorbent and 2 mL of the sample solution were used. Results are shown at a sample name "BSA solution" in Table 1. Both the aminated cellulose nanofibers exhibited higher selective ET adsorption ability in the copresence of albumin (BSA) than the poly(ε-lysine)-cellulose beads.

As described hereinabove, the ET adsorbents according to the present invention were shown to exhibit high selective ET adsorption ability in the copresence of a substance having a negative charge, such as an acidic protein.

It is noted that, as an ET adsorbent capable of selectively removing ET in the copresence of an acidic protein such as BSA, for example, the polyethyleneimine-immobilized regenerated cellulose fibers are known (Non-Patent Literature 2). However, as a result of further analysis by the present inventors, it has been shown that elution of an eluting substance composed of unknown component(s) (possibly derived from component(s) used for spinning of a regenerated fiber) does not stop upon use of the polyethyleneimine-immobilized regenerated cellulose fibers, which makes it difficult to practically use the fibers as an ET adsorbent. On the other hand, the ET adsorbent of the present invention does not cause elution of such an eluting substance, and can be suitably used as an ET adsorbent. That is, the ET adsorbent of the present invention is a significantly excellent ET adsorbent even as compared with the polyethyleneimine-immobilized regenerated cellulose fibers.

TABLE 1

| | Before treatment | | | | | | After treatment poly(ε-lysine)-cellulose beads (AEC 0.3 meq/g) | | |
|---|---|---|---|---|---|---|---|---|---|
| | Sample | LPS | | Adsorption conditions | | | Residual LPS | LPS adsorption | Protein adsorption |
| Sample name | concn. mg/mL | concn. EU/mL | pH | Ionic strength | Time h | Temp. ° C. | concn. EU/mL | rate % | rate % |
| Phosphorylated polysaccharide aqueous solution | 31 | 30 | 6.8 | <0.1 | 4 | 50 | 2.1 | 93.0 | — |
| | 31(*) | 25.2 | 7.0 | 0.1 | 2 | 25 | 0.25 | 99.0 | — |
| Collagen peptide solution | 30 | 26 | 7.0 | 0.2 | 2 | 50 | 0.11 | 99.6 | 8.0 |
| BSA solution | 0.5 | 20 | 7.0 | 0.2 | 2 | 30 | <0.01 | >99.9 | About 42 |

TABLE 1-continued

|  | After treatment | | | | | |
| --- | --- | --- | --- | --- | --- | --- |
|  | PEI-cellulose nanofibers (0.6 meq/g) | | | EDA-cellulose nanofibers (1.5 meq/g) | | |
| Sample name | Residual LPS concn. EU/mL | LPS adsorption rate % | Protein adsorption rate % | Residual LPS concn. EU/mL | LPS adsorption rate % | Protein adsorption rate % |
| Phosphorylated polysaccharide aqueous solution | 2.8 0.25 | 90.7 99.0 | — — | 2.5 0.20 | 91.7 99.2 | — — |
| Collagen peptide solution | 0.15 | 99.4 | 8.0 | 0.10 | 99.6 | 6.0 |
| BSA solution | <0.01 | >99.9 | <1 | <0.01 | >99.9 | <1 |

Batch method, 2 mL of Sample and 0.2 wet-g of Adsorbent (*), Treatment for 5 min at 90° C., for Decomposition of Limulus reaction false-positive substances Concn., Concentration Temp., Temperature <3-4> Evaluation of ET(LPS) Adsorption Ability in Fibrous Viscous Polymer Solution <3-4-1> Evaluation of ET(LPS) Adsorption Ability in Phosphorylated Polysaccharide Solution Regarding the Cell-EDA, ET adsorption tests were performed by the batch method for various reaction times (stirring times) by using a phosphorylated polysaccharide-containing sample solution (prepared by mixing 10 ml of a phosphorylated polysaccharide solution and 10 ml of a 0.02 M phosphate buffer (pH: 6.0, $\mu$=0.2) to adjust the concentration of phosphorylated polysaccharide to 1.55%; containing LPS in an amount of 25 EU/mL in terms of standard LPS (*E. Coli*-UKT-B)), to evaluate ET(LPS) adsorption ability. In the batch method, 0.2 wet-g of the adsorbent and 2 mL of the sample solution were used, and the temperature was 30° C. Results are shown in Table 2. In any reaction time (stirring time), the Cell-EDA exhibited a high LPS adsorption rate.

TABLE 2

Reaction-time dependent evaluation of LPS removal ability in phosphorylated polysaccharide solution

| Time (h) | EDA-cellulose nanofibers LPS adsorption rate (%) |
| --- | --- |
| 1 | >99 |
| 3 | >99 |
| 6 | >99 |
| 24 | >99 |

Additionally, regarding each adsorbent (Cell-PEI, Cell-EDA, and poly($\varepsilon$-lysine)-cellulose beads), ET adsorption tests were performed by the batch method using the phosphorylated polysaccharide-containing sample solution under conditions described in Table 1, to evaluate ET(LPS) adsorption ability. In the batch method, 0.2 wet-g of the adsorbent and 2 mL of the sample solution were used. Results are shown at a sample name "phosphorylated polysaccharide aqueous solution" in Table 1. Both the aminated cellulose nanofibers exhibited high ET adsorption ability in the copresence of phosphorylated polysaccharide.

<3-4-2> Evaluation of ET(LPS) Adsorption Ability in Collagen Solution

Regarding each adsorbent (Cell-PEI and poly($\varepsilon$-lysine)-cellulose beads), ET adsorption tests were performed by the batch method using a collagen-containing sample solution (prepared by dissolving 1.5 g of collagen peptide powder in 40 mL of buffer (pH 7.0, $\mu$=0.2); LPS (*E. Coli* UKT-B Lot. TFJ5099): 26 EU/mL), to evaluate selective ET(LPS) adsorption ability. In the batch method, 0.2 wet-g of the adsorbent and 2 mL of the sample solution were used. Results are shown at a sample name "collagen peptide solution" in Table 1. Both the aminated cellulose nanofibers exhibited high selective ET adsorption ability in the copresence of collagen.

<3-4-3> Evaluation of ET(LPS) Adsorption Ability in Gelatin Solution and Porcine Collagen Solution Regarding each adsorbent (Cell-PEI and poly($\varepsilon$-lysine)-cellulose beads), ET adsorption tests were performed by the batch method using a gelatin or porcine collagen-containing sample solution under conditions described in Table 3, to evaluate selective ET(LPS) adsorption ability. Results are shown in Table 3. The aminated cellulose nanofiber (Cell-PEI) exhibited high selective ET adsorption ability in the copresence of gelatin or porcine collagen.

TABLE 3

| | Before treatment | | Adsorption conditions (Stirring: 200 rpm. 2 h) | | | After treatment | | | | | |
|---|---|---|---|---|---|---|---|---|---|---|---|
| | | | | | | EDA-cellulose nanofibers AEC: 1.5 meq/g | | | poly(ε-lysine) cellulose beads AEC: 0.6 meq/g | | |
| | | | | Amount | | LPS removal ability | | | LPS removal ability | | |
| Name | Sample concn. mg/mL | LPS concn. EU/mL | Amount of sample mL | of adsorbent wet-g | Treatment temp. °C. | Residual LPS amount (EU/mL) | LPS adsorption rate (%) | Sample adsorption rate (%) | Residual LPS amount (EU/mL) | LPS adsorption rate (%) | Sample adsorption rate (%) |
| LPS | — | 50 | 12 | 1.2 | 25 | <0.01 | >99.9 | — | <0.01 | >99.9 | — |
| Gelatin (for biochemical use) aqueous solution | 30 | 110 | 12 | 1.2 | 50 | 22.50 | 83 | 9 | 66.80 | 53 | 21.3 |
| | 5 | 18 | 4 | 0.2 | 50 | <0.01 | >99.9 | 9.5 | <0.01 | >99.9 | 25.5 |
| Gelatin (edible) acid solution | 10 | 14 | 4 | 0.2 | 25 | 2.97 | 78.2 | 7.5 | 11.6 | 14.7 | 15.3 |
| | | | 4 | 0.2 | 50 | 0.10 | 99.3 | 8.5 | 2.16 | 84.1 | 16.2 |
| Porcine collagen aqueous solution | 1 | 0.21 | 4 | 0.2 | 25 | 0.03 | 85.7 | 8.3 | 0.05 | 76.2 | 11.9 |

Concn., Concentration
Temp., Temperature

As described hereinabove, the ET adsorbents according to the present invention were shown to exhibit high ET adsorption ability or high selective ET adsorption ability in highly viscous samples, such as fibrous viscous polymer solutions.

INDUSTRIAL APPLICABILITY

According to the present invention, there can be provided an ET adsorbent having high ET adsorption ability. Particularly, according to an embodiment of the present invention, there can be provided an ET adsorbent capable of selectively removing ET in the copresence of a substance exhibiting a negative charge, such as an acidic substance. Thus, by using the ET adsorbent provided by the present invention, ET can be removed from a liquid containing ET. Particularly, according to an embodiment of the present invention, by using the ET adsorbent provided by the present invention, ET can be selectively removed from a liquid containing ET and a substance exhibiting a negative charge.

The invention claimed is:

1. An endotoxin adsorbent, comprising:
a cellulose nanofiber having an amino group.

2. The endotoxin adsorbent according to claim 1, wherein the amount of the amino group in the cellulose nanofiber is from 0.05 to 3.0 meq/dry-g.

3. The endotoxin adsorbent according to claim 1, wherein the cellulose nanofiber has an average fiber diameter of from 1 to 1000 nm.

4. A method for producing the endotoxin adsorbent according to claim 1, the method comprising:
a step of introducing an amino group into a cellulose nanofiber.

5. A method for removing endotoxin, the method comprising:
contacting the endotoxin adsorbent according to claim 1 with a liquid containing endotoxin.

6. A method for producing a liquid from which endotoxin has been removed, the method comprising:
contacting the endotoxin adsorbent according to claim 1 with a liquid containing endotoxin.

7. A method for removing endotoxin, the method comprising:
contacting the endotoxin adsorbent according to claim 1 with a liquid containing a target substance and endotoxin.

8. A method for producing a liquid that contains a target substance and from which endotoxin has been removed, the method comprising:
contacting the endotoxin adsorbent according to claim 1 with a liquid containing the target substance and endotoxin.

9. The method according to claim 7, wherein the target substance is a substance exhibiting a negative charge.

10. The method according to claim 7, wherein the target substance is a protein having an isoelectric point of from 4.0 to 10.5.

11. The method according to claim 8, wherein the target substance is a substance exhibiting a negative charge.

12. The method according to claim 8, wherein the target substance is a protein having an isoelectric point of from 4.0 to 10.5.

13. The endotoxin adsorbent according to claim 1, wherein the amount of the amino group in the cellulose nanofiber is from 0.1 to 2.0 meq/dry-g.

* * * * *